United States Patent [19]

Kreuzburg et al.

[11] 4,185,029

[45] Jan. 22, 1980

[54] METHOD OF PREPARING ORTHOSILICIC ACID ALKYL ESTERS

[75] Inventors: Gerhard Kreuzburg, Niederkassel; Arnold Lenz, Cologne-Stammheim; Walter Rogler, Bonn, all of Fed. Rep. of Germany

[73] Assignee: Dynamit Nobel Aktiengesellschaft, Troisdorf, Fed. Rep. of Germany

[21] Appl. No.: 867,212

[22] Filed: Jan. 5, 1978

Related U.S. Application Data

[62] Division of Ser. No. 706,864, Jul. 19, 1976, Pat. No. 4,113,761.

[30] Foreign Application Priority Data

Jul. 19, 1975 [DE] Fed. Rep. of Germany ....... 2532473
Jul. 19, 1975 [DE] Fed. Rep. of Germany ....... 2532475
Jul. 19, 1975 [DE] Fed. Rep. of Germany ....... 2532476

[51] Int. Cl.$^2$ .............................................. C07F 7/04
[52] U.S. Cl. ...................... 260/448.8 A; 260/448.8 R
[58] Field of Search ................................... 260/448.8 A

[56] References Cited

U.S. PATENT DOCUMENTS

| 3,627,807 | 12/1971 | Bleh et al. | 260/448.8 A |
| 3,803,197 | 11/1974 | Anderson et al. | 260/448.8 A |

*Primary Examiner*—Paul F. Shaver
*Attorney, Agent, or Firm*—Sprung, Felfe, Horn, Lynch & Kramer

[57] ABSTRACT

A process for preparing an orthosilicic acid tetraalkyl ester having 2 to 6 carbon atoms in the ester group which comprises contacting metallic silicon with an alcohol corresponding to the ester group in the presence of the corresponding alkali alcoholate:

A. in the presence of a surface active substance;
B. in the presence of a compound containing a methoxy group; or
C. under pressure at a temperature above the boiling point of the reaction mixture.

5 Claims, No Drawings

ମETHOD OF PREPARING ORTHOSILICIC ACID ALKYL ESTERS

This is a division of application Ser. No. 706,864, filed July 19, 1976, now U.S. Pat. No. 4,113,761, issued Sept. 12, 1978.

BACKGROUND OF THE INVENTION

1. Field of the Invention

This invention relates to a process for preparing orthosilicic acid tetraalkyl esters having 2 to 6 carbon atoms in the ester group. More especially, this invention relates to a process for preparing such orthosilicic tetraalkyl esters which process is characterized by exceptionally improved volume-time yields. This invention is particularly directed to a process for preparing such an orthosilicic acid tetraalkyl ester wherein the process is carried out in the presence of a surface active substance or a compound containing a methoxy group or is carried out under pressure at a temperature above the boiling point of the reaction mixture. The invention is concerned especially with methods for obtaining orthosilicic acid alkyl esters in higher volume-time yields than has been provided by former methods.

2. Discussion of the Prior Art

It is known to prepare orthosilicic acid tetraethyl esters in accordance with West German Pat. No. 1,768,781 by reacting metallic silicon with ethanol in the presence of high-percentage alkali ethylate solutions. This method has the disadvantage that relatively low volume-time yields are achieved by the application thereof.

The above-mentioned disadvantages are offset to a certain extent by the method of West German Pat. No. 1,793,222. In this method the reaction is performed in the presence of the desired orthosilicic acid tetralkyl ester. This brings about a lower concentration of the alkali alcoholates in the reaction mixture.

Both methods are very well suited for the preparation of silicic acid tetramethyl ester. In the preparation of silicic acid tetraethyl ester and of the higher esters, however, difficulties are encountered which result in a reduction of the material yield and of the volume-time yield. The causes of these difficulties remain unexplained to this date.

However, in the preparation of silicic acid tetraethyl ester and the higher esters, with the silicon placed first in the reactor, the speed of the reaction diminishes constantly in the course of the reaction, and the components do not react completely, for this reduction of speed is more rapid than the reduction of the concentration of the components. In the preparation of silicic acid tetraethyl ester, for example, the result is that only about 40% of the silicon charged enters the reaction, and then, despite an excess of ethanol, the reaction comes to a halt.

While not wishing to be bound by any theory, it is believed by some that the decrease of the speed of reaction during the process is explainable in that products form during the process which adversely affect the surface of the metallic silicon. This adverse affect on the surface of the silicon, it is believed, is eliminated pursuant to the invention.

It is an object of this invention, therefore, to provide a process which speeds the course of the reaction of metallic silicon with a $C_2$–$C_6$ alcohol en route to the preparation of orthosilicic acid tetraalkyl esters having 2 to 6 carbon atoms.

SUMMARY OF THE INVENTION

Broadly, this invention contemplates a process for preparing an orthosilicic acid tetraalkyl ester having 2 to 6 carbon atoms in the ester group which comprises contacting metallic silicon with an alcohol corresponding to the ester group in the presence of the corresponding alkali alcoholate:

A. in the presence of a surface active substance;
B. in the presence of a compound containing a methoxy group; or
C. under pressure at a temperature above the boiling point of the reaction mixture.

It has been observed, in accordance with this invention, that improved volume-time yields are effected if the preparation of the orthosilicic acid tetraalkyl ester is performed either (A) in the presence of a known surface active substance, and/or (B) in the presence of a compound containing a methoxy group and/or (C) by performing the reaction under pressure at a temperature above the boiling point of the reaction mixture. It has been observed that no disadvantageous effect is imparted to the surface of the silicon reactant if the process is carried out in such a manner. An increase in the speed of the reaction is effected surprisingly. For instance, when the process is carried out under pressure at a temperature above the boiling point of the reaction mixture, the increase in the speed of the reaction is greater than average in comparison with known thermodynamic influences.

The compounds containing methoxy groups and the surface active substances can be added at any time during the reaction. If they are added at a time when the speed of the reaction has already greatly diminished an increase of the speed is soon obtained which is considerably greater than that which prevailed at the onset of the pure ethyl ester reaction. This increase cannot be explained simply on the basis of a transesterification resulting in a parallel formation of methyl ester from methanol and the metallic silicon, because the speed achieved in the reaction is greater than the sum of these individual reactions.

The addition of the surface active substances at the onset of the reaction causes the reaction to take place between silicon and alcohol without appreciable impediments, and the difficulties described above are not encountered or encountered only to a reduced extent.

Suitable surface active substances useful herein include known wetting agents, emulsifiers, penetrating agents or flotation agents, provided that they do not enter into conflicting reactions with one of the reactants. The amount to be added depends on the nature of the substances used. In general, small amounts, amounting to 2.5 to 0.01% by weight Si and generally about 1% of the weight of the metallic silicon charged suffices, as long as it is sufficient to cover the surface of the silicon metal.

The surface active substances useful in accordance with the invention also include nitrogen-containing organic bases, such as cyclic tertiary or secondary amines, especially $C_1$–$C_8$ tertiary or secondary cyclic amines (e.g., quinoline, isoquinoline, pyridine, piperidine) or diarylsulfoxides, dialkylenesulfoxides, and dialkylthioureas. The use of these compounds has the additional advantage that they more or less greatly counteract the undesirable secondary reaction of the formation of alkanes and water, which will be described further below.

If flotation agents are used as surface active substances, it can happen, especially if foaming agents are also used, that the reaction mixture will foam up, and most of the metallic silicon will gather together with the foam in the upper part of the reaction vessel. It is then desirable to allow the foam to overflow together with the silicon through a suitable overflow device into a second reaction vessel, and there to continue the reaction by the addition of a defoaming agent and freshly added alcohol, alcoholate and, if desired, silicic acid tetraalkyl ester. The silicon that overflows no longer displays the above described reluctance to enter the reaction, and reacts like freshly introduced silicon.

Methanol, alkali methylates and silicic acid methyl ester are especially suitable as compounds containing methoxy groups. Of these, the alkali methylates, such as sodium methylate, for example, have shown the strongest action. The amount to be added can be between 5 and 20%, preferably between 8 and 15%, of the weight of the metallic silicon, reckoned as $-OCH_3$ groups. The alkali methylates can also be added in solid form.

In the reaction between silicon and alcohols, it is known that hydrogen forms in statu nascendi and to a slight extent hydrogenates the alcohol present, to form alkanes and water (cf. Houben-Weyl VI/2, p. 100). This water reacts with the catalyst, diminishing its activity, and it reacts also with the silicic acid ester that has formed in the alkaline reaction solution. If the reaction is performed under pressure, one would have to expect that this hydrogen gas, which is not carried off in the reaction is performed under pressure, would shift the reaction equilibrium more towards the starting components. Surprisingly, however, this is not the case.

The higher the pressure is, the more pronounced is the reaction between the hydrogen formed in the reaction and the alcohols whereby water is formed. This intensified formation of water theoretically acts against any increase in the speed of the reaction in the case of the reaction between silicon and alcohol under pressure and at high temperatures. Actually, however, the opposite is the case.

The reaction between silicon and alcohol in the presence of alkali alcoholates generally starts up at temperatures around 160° C. Up to this temperature the system can be kept closed if it is operated under pressure. After the reaction starts up, the exothermia of the reaction makes additional heat input unnecessary. After the onset of the reaction, the increase in the pressure is no longer proportional to the increase of the reaction temperature but overproportional due to the hydrogen that is formed in the reaction. In principle, one can perform the reaction at pressures up to 50 atmospheres gauge. In general, the desired pressure depends on the apparatus available. When the desired pressure is achieved, it can easily be kept constant by letting off the newly formed hydrogen through suitable valves. Letting off the hydrogen permits control of the reaction temperature. Since a mixture of alcohol and silicic acid ester is also escaping, evaporation heat is also being removed from the system.

The above-described release of the alcohol-silicic acid mixture also permits the process to be performed continuously under pressure. In this case it is desirable to feed in the silicon as a dispersion in alcohol or silicic acid ester. The amount of the alcohol used in that case, and the ratio of silicon to alcohol, is governed by the amount of alcohol-silicic acid ester mixture that is withdrawn. Essential to a continuous process is the establishment of a temperature at which the reaction mixture will boil at the selected pressure. The boiling point of the mixture can be controlled through the alcohol content.

In principle, the reaction is performed in the manner described in German Pat. Nos. 17 68 781 and 17 93 222, the disclosures of which are hereby incorporated herein as references. The concentration of the individual components in the system can vary within wide limits. It is advantageous, however, to select the proportions such that an easily stirred mixture is obtained, and the ethylate is present as a solute in the alcohol. Basically, however, one can operate without an excess of silicon in the system and feed in the silicon together with the alcohol only in the amount that will react per unit of time.

The reaction can be performed discontinuously or continuously. The separation of the reaction product from the reaction mixture is preferably performed by distillation.

The water that forms in small amounts due to the secondary reaction described above reacts with the catalyst, which thus loses some of its activity, and also with the silicic acid ester formed in the alkaline reaction solution. The removal of the water can be accomplished by partially distilling the reaction mixture, using as the withdrawing agent the hydrogen gas that is forming, or also an inert gas, such as nitrogen for example, which is additionally passed through the reaction vessel.

The water-containing, gaseous distillation products are at the same time condensed in such a manner that the condensate will be unable to flow back directly into the reaction vessel. The return of the distillate to the reaction vessel is then accomplished, if desired, by means of appropriate water withdrawing agents.

If, in the case of a continuous procedure, the methoxy groups in the form of the methanol that is formed are removed from the reaction mixture during the distillative separation of the ester, they must be replaced continually by the addition of fresh material. If the mixed esters that form due to the addition of the compounds containing methoxy groups are not desired, the distillative separation is performed by means of a column in which the methoxy groups are carried away in the form of methanol as a result of transesterification with excess ethanol.

The small amount of catalyst that is consumed during the reaction as described above can be replaced together with the alcohol feed or with the feed of the surface active substance.

Pure silicon as well as ferrosilicon or other silicon alloys containing more than 50% silicon can serve as the metallic silicon to be used in accordance with the invention. The grain size of the silicon or silicon alloys should be no greater than 100μ. Preferably it is between 2 and 20μ.

In order to more fully illustrate the nature of the invention and the manner of practicing the same, the following examples are presented:

EXAMPLE 1 (for purposes of comparison)

In a one-liter stirring vessel having an anchor stirrer running along the walls and equipped with a temperature measuring means and a reflux condenser from whose open end the hydrogen that forms during the reaction is removed and measured by means of a gas meter, 200 grams of FeSi of a fineness between 15 and $20\mu$, 400 grams of silicic acid tetraethyl ester, and 20 grams of sodium ethylate are combined. After the addition of 100 grams of ethyl alcohol, the mixture is heated to the refluxing temperature.

After the reflux temperature is reached, an hourly formation of approximately 6 liters of hydrogen is established. This corresponds to a volume-time yield of 28.5 grams of silicicic acid tetraethyl ester per liter per hour.

EXAMPLE 2

In a one-liter stirring autoclave equipped with a temperature measuring means and a pressure-tight reflux condenser at whose upper end there is provided a regulating valve for controlling the pressure and the removal of the hydrogen, 200 grams of FeSi of a fineness between 15 and $20\mu$, 400 grams of silicic acid tetraethyl ester, 20 grams of sodium ethylate and 100 grams of ethyl alcohol are combined. The autoclave is preheated to 150° C.; then the heating system is turned on. Then the temperature increases within 5 minutes to 185° C. while the pressure rises to about 10 atmospheres absolute. This pressure is maintained constant by letting off the hydrogen that continues to form, through the balancing valve and through the gas meter. The reaction was sustained for another 20 minutes, the temperature rising to 198° C. By the end of these 20 minutes a total of 21 liters of hydrogen had been let off. The amount of hydrogen formed corresponds to a volume-time yield of about 280 grams of silicic acid tetraethyl ester per liter per hour. This proves that the method of the invention produces a considerable increase of the volume-time yield in comparison with the known methods of Example 1.

EXAMPLE 3

In a one-liter stirring vessel equipped with an anchor stirrer running along the walls, an insulated distillation column, an input connection, and a system for measuring the temperature in the liquid, 500 grams of silicic acid tetraethyl ester, 250 g of FeSi and 12.5 g of sodium ethylate are combined. After the boiling temperature is reached, ethanol is fed in. The reaction that starts results in esterification at a rate indicated by the formation of hydrogen gas at 6 liters of hydrogen gas per hour. After one hour of operation, the rate of the reaction drops to from 2 to 3 liters $H_2/h$.

Then 25 g of silicic acid tetramethyl ester (=8 wt-% methoxy groups with respect to FeSi) is added to the hot reaction mixture. The formation of hydrogen immediately increases to 24 l/h and remains at this level for several hours while the addition of ethanol continues. This corresponds to a 300% increase in the speed of the reaction.

After the addition of another 10 g of silicic acid methyl ester (total addition approximately 11% methoxy groups), the rate of the reaction can be increased to 32 l $H_2/h$ for several hours while continuing the ethanol feed.

When the ethanol feed is terminated, the excess alcohol reacts away, and a boiling point of 163° C. establishes itself. This boiling point is only slightly below the theoretical boiling point of the tetraethyl ester of 165° C. The reduction of the boiling point is to be attributed to a small content of mixed esters.

After several hours of shut-down, the mixture was again heated to the boiling point and the ethanol feed was resumed, and the same rate of reaction was achieved as before the ethanol feed was shut off.

EXAMPLE 4

The procedure was the same as in Example 3, except that sodium methylate was added instead of silicic acid tetramethyl ester, in the amount of 40 grams (=9 wt.-% methoxy groups). 180 liters of hydrogen gas per hour developed momentarily; after the reaction had been sustained for several hours at a uniform rate of ethanol feed, the reaction rate, as measured by the formation of hydrogen, decreased to from 80 to 100 liters of hydrogen gas per hour. Upon the addition of another 20 g of sodium methylate, the hydrogen gas formation could be increased again to from 180 to 200 l/h.

What is claimed is:

1. A process for preparing an orthosilicic acid tetraaalkyl ester having 2 to 6 C atoms in the ester group which comprises contacting metallic silicon with an alcohol corresponding to the ester group in the presence of the corresponding alkali alcoholate and orthosilicic acid tetraalkyl ester having 2 to 6 carbon atoms in the ester group under pressure and in the liquid phase at a temperature above the boiling point of the reaction mixture.

2. A process according to claim 1 wherein the process is performed at a temperature between 160° and 210° C. under pressure up to 50 atmospheres gauge.

3. A process according to claim 2 wherein the pressure is regulated by bleeding off hydrogen formed during the reaction.

4. A process according to claim 2 wherein the process is conducted continuously, silicon is introduced into the reactor in the form of a dispersion in alcohol or in the desired silicic acid ester and the formed ester is withdrawn together with hydrogen formed in the process in a mixture with alcohol.

5. A process according to claim 1 wherein the reaction mixture initially contains orthosilicic acid tetraalkyl ester having 2 to 6 carbon atoms in the ester group before the metallic silicon is reacted with the alcohol.

* * * * *

UNITED STATES PATENT AND TRADEMARK OFFICE
CERTIFICATE OF CORRECTION

PATENT NO. : 4,185,029
DATED : January 22, 1980
INVENTOR(S) : Gerhard Kreuzburg, Arnold Lenz, Walter Rogler It is certified that error appears in the above-identified patent and that said Letters Patent are hereby corrected as shown below:

On the cover page, under "References Cited, U.S. Patent Docments", the date for the Anderson et al patent should be --4/74--.

Signed and Sealed this

Tenth Day of June 1980

[SEAL]

Attest:

SIDNEY A. DIAMOND

Attesting Officer

Commissioner of Patents and Trademarks